(12) United States Patent
Bogas Cardeñosa

(10) Patent No.: US 7,288,268 B2
(45) Date of Patent: Oct. 30, 2007

(54) FORMULATION FOR THE TREATMENT OF OBESITY

(76) Inventor: Antonio Miguel Bogas Cardeñosa, Plaza de Capuchinos, 1 E-14001 Córdoba (ES)

(*) Notice: Subject to any disclaimer, the term of this patent is extended or adjusted under 35 U.S.C. 154(b) by 414 days.

(21) Appl. No.: 10/454,538

(22) Filed: Jun. 5, 2003

(65) Prior Publication Data

US 2004/0247694 A1    Dec. 9, 2004

(51) Int. Cl.
*A61K 9/14* (2006.01)
(52) U.S. Cl. ..................................... 424/489
(58) Field of Classification Search .................. 424/489
See application file for complete search history.

(56) References Cited

OTHER PUBLICATIONS

Boletin Informativo, 1994, Cento Regional de Farmacovigilancia e Informacion Terapeutica de Canarias, vol. 2 No. 5 pp. 1-4.*
Thesis: Sylvie Voisin-Dahan, "Les Substances D'Origine Animale Utilisées en Therapeutique", Université Paris V. René Descartes, Table of Contents, No. 252, (1987).
José Cabrera Forneiro and Rafael Cabrera Bonel, "Efectos Secundarios y Tóxicos de los Psicofármacos", Su tratamiento, (ROCHE), pp. 5-22, (1983).
A. del Rio Vázquez et al., "Result of the Administration of High Doses of Bumetanide to Patients With Chronic Renal Failure Who Are On A Program of Hemodialysis", Medicina Clinica, Vo. 72, No. 25, pp. 70-73, (Jan. 1979).
D.A. Silk, Progress Report, "Peptide Absorption in Man", Gut, vol. 15, pp. 494-501, (1974).
K.E. Webb, Jr., "Amino Acid and Peptide Absorption from the Gastrointestinal Tract", Federation Proceedings, vol. 45, No. 8, pp. 2268-2271, (Jul. 1986).
Thesis: Jean-Cleaude Dahan, "Les Substances D'Origine Animale Utilisées en Therapeutique", Université Paris V René Descartes, No. 251, (1987).
Laboratoire Industriel de Biologie report citing "Hypothalamic Hormones" (Serono Symposia), Academic Press Inc. London, last page, (1975).
Martine Allain-Regnault, "Une nouvelle chimie du cerveau", La Revue TRIANGLE: Journal Sandoz des Sciences Médicales, deuxieme trimestre, vol. XVI, No. 2, p. 39, (1976).
John A. Owen, Jr., "*Focus on bumetanide. An extremely potent diuretic with minimal toxicity*", Hospital Formulary Press, pp. 933-935 (Sep. 1981).
Alastair J. J. Wood, "Use of Benzodiazepines in Anxiety Disorders", The New England Journal of Medicine, pp. 1398-1405, (May 13, 1993).
Laboratoire Industriel de Biologie "L'opotherapie", no date shown.
Institut Français de Recherches et Essais Biologiques, Lot No. 7007, (May 10, 1976).
Archivo Bibliografico del Ilustre Colegio de Medicos de Cordoba, 44-45 (Nov. 1985)—English translation.
Archivo Bibliografico del Ilustre Colegio de Medicos de Cordoba, 44-45 (Nov. 1985).
Spanish System of Drug Control, Informative Bulletin Regional Center of Drug Control and Therapeutic Information of Canary Islands, vol. 2, No. 5, 1994.

* cited by examiner

*Primary Examiner*—Alton Pryor
(74) *Attorney, Agent, or Firm*—Wenderoth, Lind & Ponack, L.L.P.

(57) ABSTRACT

The present invention refers to a formulation for a slimming treatment comprising in certain quantities: hypothalamus powder, hypophysis powder, thyroid powder, suprarenal cortex powder and pancreas powder, and other polyglandular opotherapic extracts such as extract of ovary or testicle; said slimming treatment being evaluated and optimised thanks to an exponential mathematical model which models the accumulated weight loss of a patient by means of a differentiation and separation of the slimming effect due to the set of factors depending on the applied slimming treatment and, on the other hand, of the slimming effect due to the set of factors depending on the typology of the patient trying to slim.

2 Claims, 5 Drawing Sheets

US 7,288,268 B2

FORMULATION FOR THE TREATMENT OF OBESITY

FIELD OF THE TECHNIQUE

The present invention falls within the field of treatments for obesity and overweight.

STATE OF THE ART PRIOR TO THE INVENTION

Obesity is a multiple aetiology problem, in the genesis of which there are many factors intervening in an isolated form or, very much more frequently, in a combined form. The involvement of so many factors is what sometimes makes it impossible to predict the result that might be obtained by means of a slimming method with a particular patient.

Moreover, surprisingly, these uncertainties contrast sharply with the profound knowledge currently had of the most intimate physiological and biochemical mechanisms intervening in the physiopathology of obesity. Thus, well known are the digestive and intestinal absorption mechanisms, the mechanisms of insulin regulation, the mechanisms of glucemia regulation (hepatic, muscular and central), the physiology and histology of adipose tissue, thyroid physiology and pathology, the physiology and pathology of the hypophysis, etc. It can be said that a fair amount is known about the phenomena inherent to glandular, tissue and cellular physiology and pathology, involved in disturbances to the adipose tissue and obesity.

A fundamental work on the absorption mechanism of oligopeptides and amino acids is: D. A. Silk Progress report. Peptide absorption in man, Gut, 1974, 15 494-501. This work reveals that there exist two essential mechanisms in peptide absorption: on the one hand the hydrolysis of peptides by brush border enzymes with the consequent absorption of amino acids released by means of specific amino acid transport systems, and on the other hand the absorption of peptides by mechanisms independent of the specific entrance of each amino acid, followed by intracellular hydrolysis.

With regard to amino acid and peptide absorption, K. E. Webb, Jr., Amino acid and peptide absorption from the gastrointestinal tract, Federation Proceedings Vol 45, no. 8 Jul. 1986, describes that the large quantity of peptide amino acids appearing in portal plasma is surprising, corresponding to more than 70% of the total quantity of portal plasma amino acids. And it is also observed that, with the exception of cysteine they are all associated with amino acids coming from diet. Therefore, if these peptidic amino acids come from diet, this great contribution will be of essential nutritional importance.

Moreover, in addition to the knowledge of the physiological mechanisms stated above, there also exists a wide-ranging knowledge of the basis on which many existing slimming formulations are founded and the principles on which the administration of different substances for slimming purposes are based. It is worth recalling, for example, that opotherapy, or treatment of insufficiencies, or absence of glands, or of organs, by means of fresh organs and/or extracts of these organs in liquid or powder form, has its roots at the end of the nineteenth century, and there currently exist opotherapic products for any tissue or organ of the body. Opotherapic products are regulated in the pharmacopoeia. An essential work on opotherapy is the doctoral thesis of Jean-Clause Dahan, *Les substances d'origine animale utilisées en therapeutique*, 1987, Université Paris V René Descartes. It is furthermore known that the role of the hypothalamus in the organism is essential, and that its most relevant function from the viewpoint of opotherapy is the regularisation of hyperphagia or exaggerated appetite in obesity (Hypothalamic Hormones (Serono Symposia) Academic Press Inc. London 1975). Opotherapic products of hypothalamus powder have recently been prepared for different purposes, as contained in *Une nouvelle chimie du cerveau*. Martine Allain-Regnault, "la Revue TRIANGLE: journal Sandoz des Sciences Médicales, deuxième trimestre 1976; volume XVI, number 2. In the case of its use for the preparation of slimming formulations, the ventrolateral nuclei or hunger nuclei are eliminated from the hypothalamus. This means that for the preparation of a formulation for a slimming treatment, a natural anorexic is available.

As potential components of slimming formulations, there exist substances such as chlorodiazepoxide, diazepam and bumetanide, which have been known and used for a long time in hospital practice. An important work on bumetanide is that of John A. Owen, Jr. MD. *Focus on bumetanide. An extremely potent diuretic with minimal toxicity* September 1981 Hospital Formulary, 933-935. Another important work on benzodiazepines is that by Alastair J. J. Wood "*Use of benzodiazepines in anxiety disorders*" The New England Journal of Medicine, May 13, 1993.

By virtue of this knowledge, it is therefore not understood why the results presently obtained with slimming treatments are so unpredictable. In theory, there are two answers: the first is that the different and profound branches of partial knowledge have not been sufficiently assembled together so far, and the second is that there exists some other aspect or aspects that are partially unknown or which have not been taken sufficiently into account. It can be concluded that both those answers are true in part, in other words, on the one hand all the partial factors have not been assembled properly and, moreover, some of the partial mechanisms have not been taken sufficiently into account when it comes to designing a slimming treatment.

Nevertheless, in spite of that knowledge of many factors that act on obesity and which therefore determine the result of a treatment for this condition, there does not exist a complete knowledge of the interrelation between those factors. For this reason, in many cases it is not known to which types of factors the success or failure of a slimming plan should be attributed, or whether it should be attributed to all of them. So, the result of a treatment against obesity continues to lie largely in the hands of chance.

Therefore, there exists a need for a method which, in the appropriate manner and magnitude, would consider all the factors intervening in obesity in order to overcome the drawbacks mentioned and be able to guarantee the desired results in its treatment.

BRIEF DESCRIPTION OF THE INVENTION

The present invention refers to a formulation for a slimming treatment comprising at least:

hypothalamus powder in a quantity between 0.01 and 0.5 mg, hypophysis powder in a quantity between 1 mg and 30 mg, thyroid powder in a quantity between 10 and 40 mg, and suprarenal cortex powder and pancreas powder in a proportion of 1:4 this slimming treatment being evaluated and optimised thanks to an exponential mathematical model which models the accumulated weight loss of a patient by means of a differentiation and separation of the set of factors depending on the applied slimming treatment and of the set of factors depending on the typology of the patient trying to slim.

DETAILED DESCRIPTION OF THE INVENTION

Figure 1:
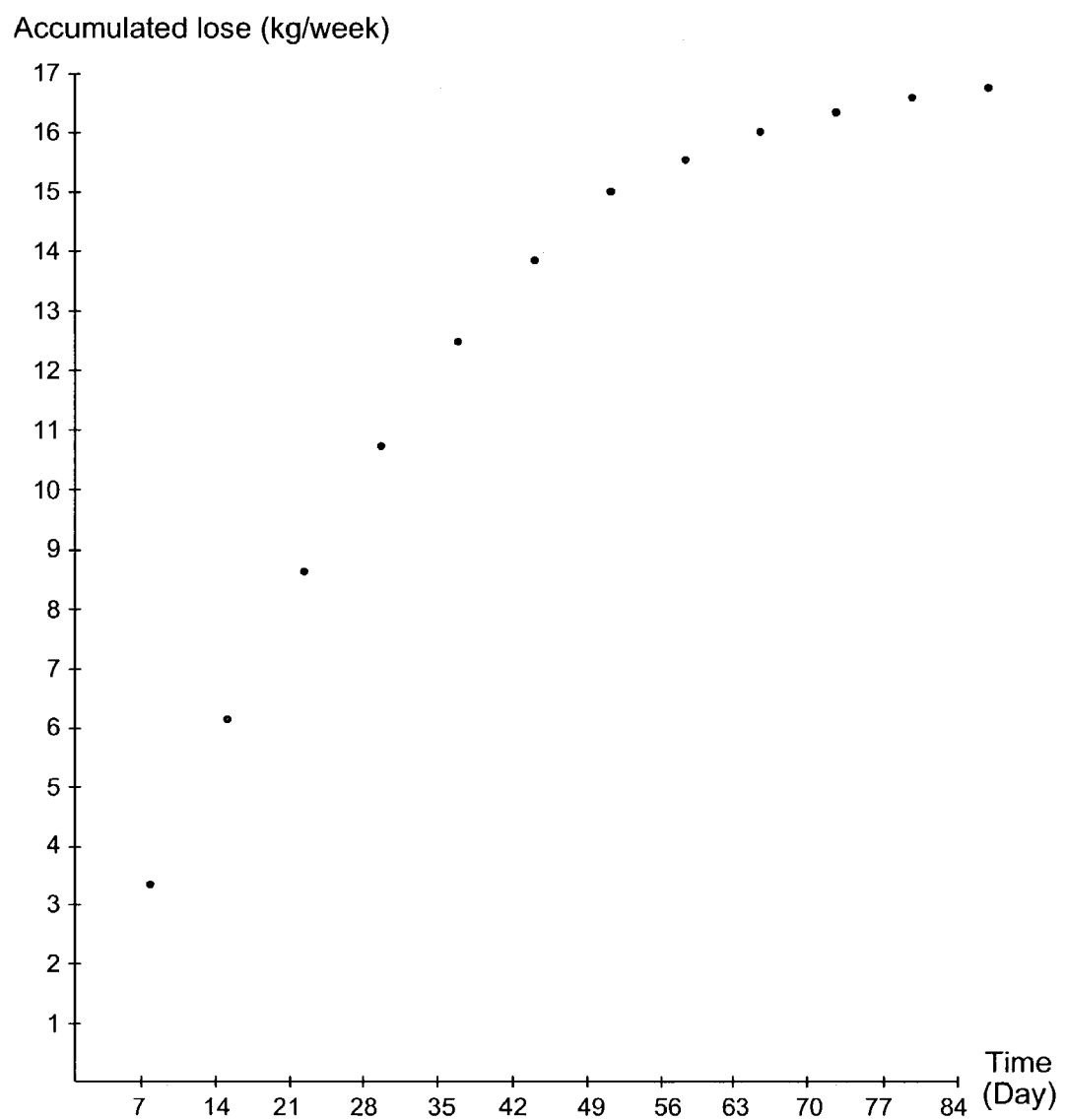
FIG. 1 is a representation in Cartesian coordinates of the cluster of points corresponding to the accumulated weekly weight loss in relation to the passing of days.

For the production of the mathematical model permitting the formulation for the slimming treatment forming the object of the invention to be evaluated and optimised, one starts from the fact that, as can be seen in Table I, among the factors that can influence obesity, some (marked with (1)) depend on the typology of the patient, while others (marked with (2)) depend on the slimming method used.

TABLE I

| Factors inherent to the organism (1) | Factors that are external or of the treatment (2) |
|---|---|
| heredity | dietary habits (eating a lot, eating quickly) |
| length of time of the obesity (hyperplasia or hypertrophic) | type of job activity |
| backgrounds of other slimming treatments | sedentarism |
| nervous typology | climatic changes |
| character | type of dietary treatment |
| degree of stress | type of medical treatment |
| backgrounds of surgical operations | type of psychological treatment |
| menarche (women) | others |
| menopause (women) | |
| others | |

This differentiation into aetiological factors (1) and (2) already implies a first and fundamental simplification of the problem.

On the other hand, one starts from research conducted with 1,800 patients, selected and distributed into 9 groups of 200 people each, according to sex, maternity and fertility, degree of stress, and type of slimming treatment applied (VLCD=Very low calorie diet), as illustrated in Table II:

TABLE II

GROUPS OF PATIENTS STUDIED 1  men, middle age, normal activity and only subject to VLCD
2  women, fertile age, childless, normal activity and only with VLCD
3  women, with children, normal activity and births without general anaesthetic (VLCD)
4  women, with children, normal activity and births with general anaesthetic (VLCD)
5  women during the menopause (VLCD)
6  women, 10 years after the menopause (VLCD)
7  men, subject to very stressful activity and VLCD
8  men, not stressed, subject to VLCD and anorexics
9  men, not stressed, subject to VLCD and ansiolytics (VLCD = Very low calorie diet)

For each patient, the weight losses achieved in each week of treatment were recorded up to a total of 12 weeks. These data, represented on Cartesian axes, with the time variable (week) on the abscissa axis and weight loss on the ordinate axis, do not reveal anything interesting.

Nevertheless, when not just the simple weight loss per week, but instead the weight loss for each week accumulated with the previous weeks is represented on the ordinate axis, then a cluster of points results which, according to the mathematical model followed for the present invention, is identified or modelled by means of a curve of exponential growth, with an attenuated growth and which tends indefinitely towards an asymptote parallel with the abscissa axis. Therefore, for each patient, the "y" variable represents the accumulated weight loss per week (stated in kilograms) on the ordinate axis, as a function of the "x" variable, which represents the time passed with the patient subject to a certain slimming treatment on the abscissa axis, up to a total of 12 weeks.

Figure 2:
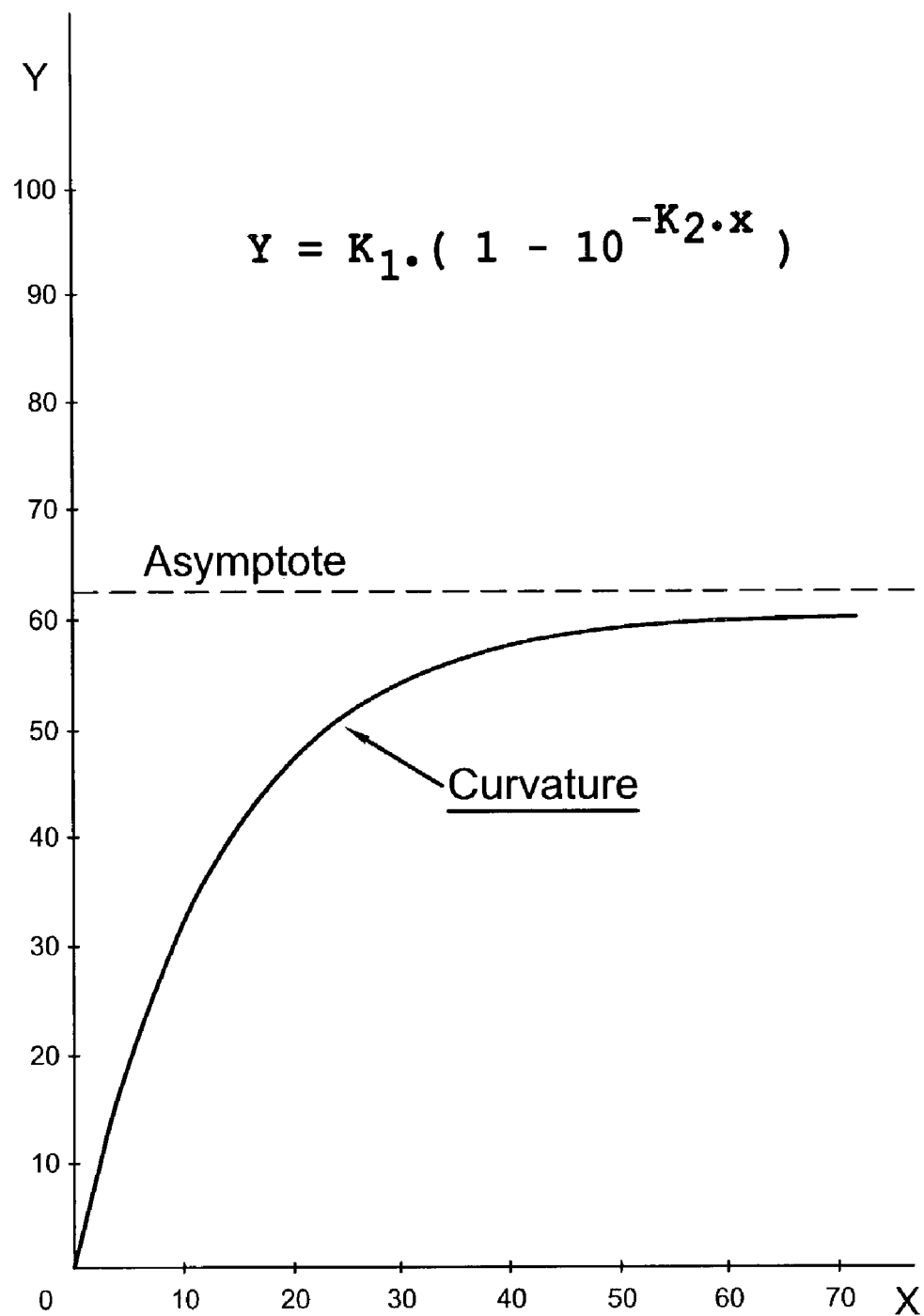
FIG. 2 illustrates a generic form of an exponential function by means of which it is intended to mathematically model the cluster of points corresponding to the accumulated weekly weight loss, in relation to the passing of days, by means of fitting the constants $K_1$ and $K_2$.

These data are illustrated for a particular case in FIG. 1, where the cluster of points can be observed, and in FIG. 2, where a generic form of an exponential function is illustrated, by means of which it is intended to mathematically model that cluster of points, through the fitting of the constants $K_1$ and $K_2$.

These curves obtained representing the accumulated weight loss each week on the ordinate, and the time passed since the start of the slimming treatment on the abscissa correspond mathematically to equations of the type $y=K_1 \cdot (1-10^{-K_2 \cdot X})$, in which $K_1$ and $K_2$ are two constants.

These types of curve are frequent and habitual in biological phenomena such as embryo growth or the growth of bacterial colonies. So, in the case of weight loss there is a phase of quick exponential weight loss, followed by a phase of slower loss until reaching the moment at which the weight loss is infinitesimal and finally stops in the zone in which the asymptote has been reached.

Such exponential functions depend on a single variable (x), but also influenced by two constants: $K_1$, which expresses the asymptote or maximum height that the curve can reach, indicating that, no matter how much time passes, no additional weight loss will occur beyond that obtained; and $K_2$, which expresses the curvature of the curve, in this case indicating the speed with which the growth in the first phase takes place, in other words, the speed with which the weight loss takes place. Each of these constants comprises or expresses a group of factors. Therefore, some factors are included in $K_1$ and thereby influence the maximum height of the curve, and others are included in $K_2$ expressing the speed with which the accumulated weight loss in the first phase grows. What "y" represents is the number of kilograms of weight lost as the days of treatment pass.

By means of studying the 9 groups of 200 patients each, stated above, and on the basis also of that described in Tables I and II, it is demonstrated that each of the two constants $K_1$ and $K_2$ is associated with one type of the factors that intervene in obesity. On the one hand, it has been verified that the factors included in $K_1$ correspond to the factors inherent to each person, which therefore depend on the characteristics of the patient, such as hormone factors, habits, etc. Each person, on account of his or her nature, possesses a maximum limit of weight loss, independent of the time during which the treatment is maintained. That maximum limit is the asymptote of the particular curve of that patient. No matter how long the treatment is kept up for, the patient will not be able to lose weight above the value represented by $K_1$.

On the other hand, it has been confirmed that a second type of factors depends on the slimming method applied, and these are the factors encompassed within $K_2$.

$K_1$ therefore encompasses hereditary factors, hormone factors, habits, etc., in other words, factors classified as (1) in Table I above.

On the other hand, the constant $K_2$ includes those factors which depend solely on the sliming method applied, since each method entails a greater or lesser speed of weight loss, depending on its efficacy and characteristics, such as type of diet, medication, exercise, etc. In other words, $K_2$ encompasses the factors classified as (2) in Table I above, among others, which can depend on the treatment. The constant $K_2$ is only affected by the different slimming power of the slimming treatment applied, and in the graph it is represented by the degree of curvature of the curve; in other words, the speed with which the curve ascends to the asymptote.

The constant $K_1$ will henceforth be known as Slimming Potential and be referred to as IB ("body") and depends exclusively on the characteristics of the patient, representing the maximum weight he or she can lose, no matter what the slimming method used and the length of time subject to treatment.

The constant $K_2$ will henceforth be known as Efficiency Index and be represented as IM (method), therefore expressing the greater or lesser speed with which a particular patent can achieve the maximum weight loss.

The curve of accumulated weight loss for each patient can therefore be represented by the equation:

$$W = IB \cdot (1 - 10^{-IM \cdot N}) \quad \text{Equation (1)}$$

in which W represents the accumulated weight loss by the patient, N is the number of weeks of treatment and IB and IM have the meaning stated above.

The value of IB can lie between 0 and infinity, since it is the maximum weight loss, so that when IB=0, W coincides with the abscissa axis, which would mean that the patient would never slim at all. This situation corresponds to an extremely thin person for whom no method could cause them to slim more. It could also represent the case of a person who is obese but incapable of slimming. These two situations are merely theoretical and do not occur in practice. On the other hand, when IB is infinite, this means that the patient would never stop slimming, in other words, they would never reach their asymptote, something which also does not occur in practice.

Figure 3:
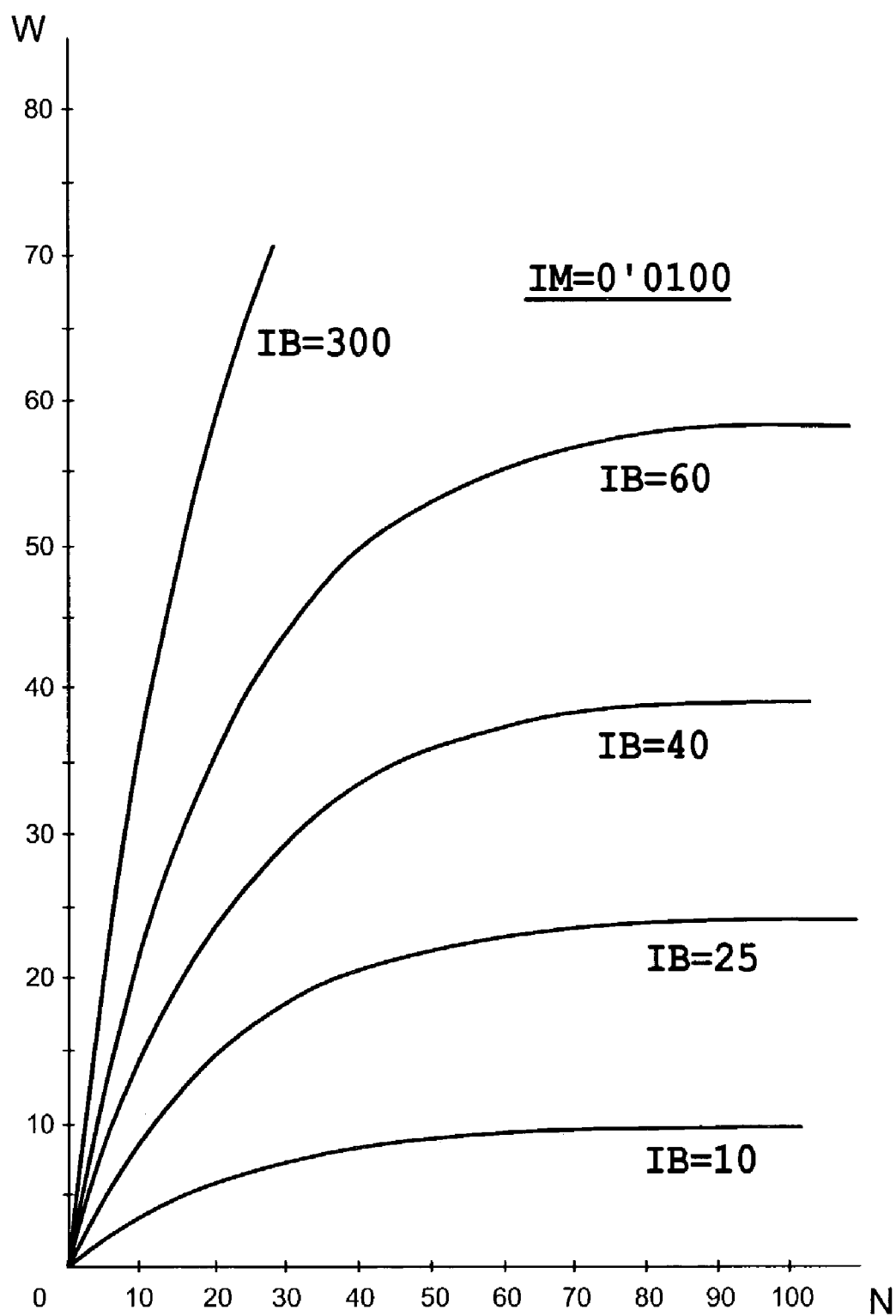
FIG. 3 represents a study of various values of IB (or Slimming Potential), each of them establishing a different asymptote or accumulated slimming limit, with IM (or Efficiency Index) remaining constant.

FIG. 3 represents a study of various values of IB (each of them establishing a different accumulated slimming asymptote or limit), with IM remaining constant.

When IM=0, the weight loss is also nil, and this would mean that the method used has an efficacy that is so low that the curve does not rise up from the abscissa axis, no matter how many weeks the treatment lasts for. This situation could occur in the case of not applying the method or, more commonly, in the case of total non-compliance of the treatment by the patient. The final motive for this situation would be complete inefficacy of the treatment, which does not occur in practice.

The situation in which IM is infinite likewise lacks any sense. This situation would occur in the case of the treatment being so effective that the maximum weight loss would be obtained in the first day of applying the slimming method, which would only be possible by means of a liposuction treatment or surgical removal of all the fat in the body.

Figure 4:
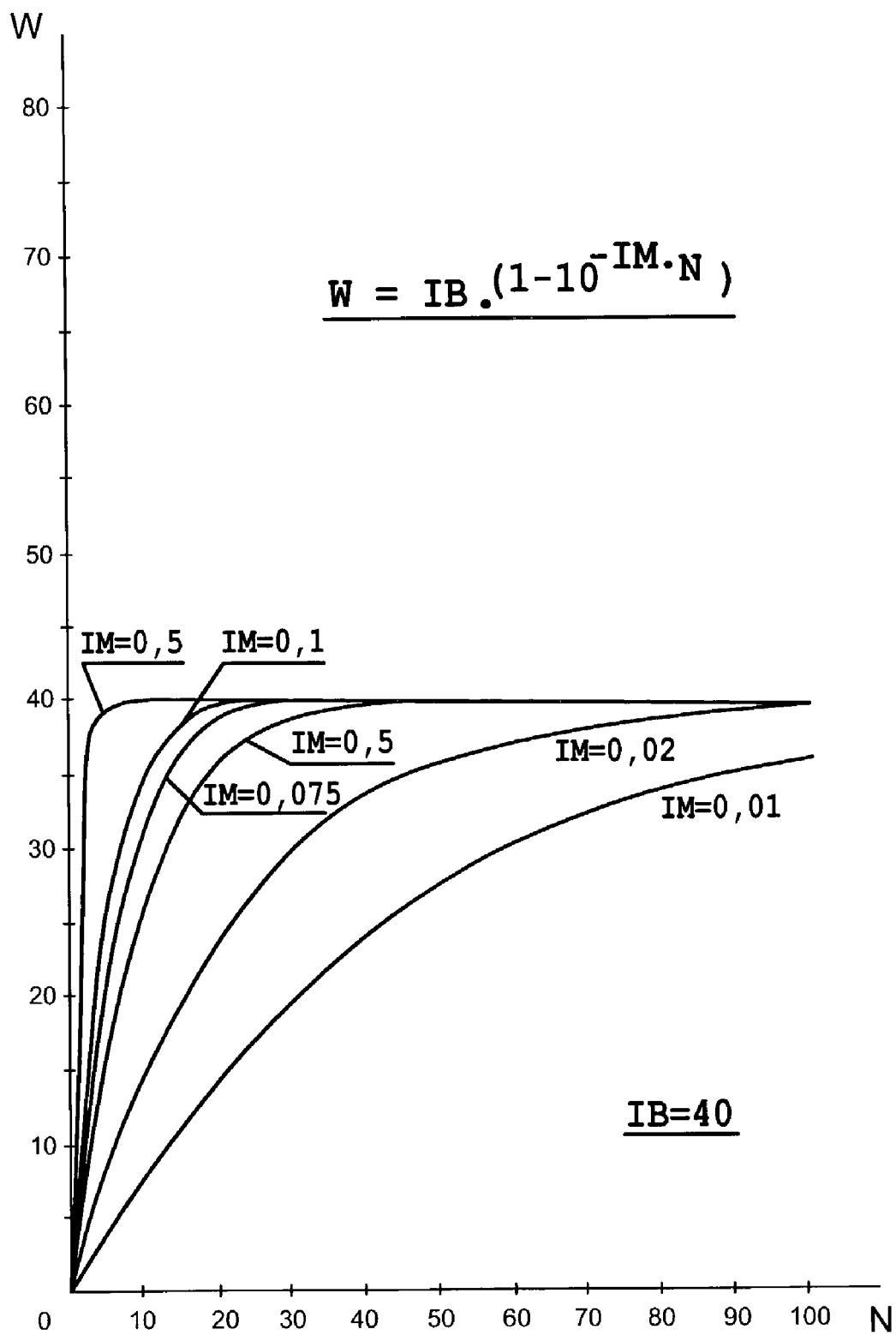
FIG. 4 represents a study of various values of IM (or Efficiency Index), each of them establishing a different curvature or speed of accumulated weight loss, with IB (or Slimming Potential) remaining constant.

FIG. 4 represents a study of various values of IM (each of them establishing a different accumulated weight loss curvature or speed), with IB remaining constant.

In practice, of course, situations occur that correspond to intermediate values, both for IB and for IM.

Table III presents by way of example a list of data on a particular patient that can be represented as a cluster of points on the Cartesian axes (No. of weeks, accumulated kilos lost) and the results to be obtained assimilating or modelling that cluster of points to the exponential mathematical model, for a particular patient:

TABLE III

| INPUT INFORMATION | | |
|---|---|---|
| Time (days) | Accumulated weight loss (kg/week) | INFORMATION TO OBTAIN |
| 7 | 3.200 | IB + IM = |
| 14 | 6.500 | exponential CURVE |
| 21 | 8.600 | |
| 28 | 10.700 | |
| 35 | 12.450 | |
| 42 | 13.880 | |
| 49 | 14.930 | |
| 56 | 15.610 | |
| 63 | 16.030 | |
| 70 | 16.360 | |
| 77 | 16.560 | |
| 84 | 16.680 | |

With the aim of finding the exponential curve defined by IB (asymptote) and IM (curvature) providing the closest possible fit to the given cluster of points, the widely known mathematical method of least squares is turned to, consisting of finding which values (in this case of IB and IM) minimise the mean square error of the curve defined by IB and IM in relation to that given cluster of points for each patient in particular who has followed a specific slimming method.

Starting from Equation (1), the ordinate of a point (or day) "i" is given by the equation:

$$W_i = IB \cdot (1 - 10^{-IM \cdot N_i}) \quad \text{Equation (2)}$$

(in which $N_i$ is the corresponding day and $W_i$ is the accumulated weight loss up to that day).

The square error ($\epsilon$) or difference squared between the set of points $W_i$ corresponding to Equation (2) and the points $W_{r_i}$ corresponding to the real data recorded by the patients will therefore be:

$$\varepsilon = \sum_{i=1}^{n}(W_i - W_{ti})^2 = \sum_{i=1}^{n}(IB \cdot (1 - 10^{-IM \cdot N}i) - W_{fi})^2 \quad \text{Equation (3)}$$

("n" being the number of days (points) to consider and $W_{fi}$ the reliable value of accumulated weight loss on day "i", calculated on the basis of the arithmetic mean of the 200 values corresponding to 200 people of a single group who accord with one of the 9 typologies of people mentioned in Table II).

In order to minimise the square error ($\varepsilon$): the first partial derivative of $\varepsilon$ (Equation (3)) with respect to IB is set equal to zero and an equation is obtained with respect to IB with the minimum error of adaptation to the theoretical curve postulated for the cluster of points resulting from the experimental data:

$$\frac{\partial \varepsilon}{\partial IB} = 2 \cdot \sum_{i=1}^{n}\{IB \cdot (1 - 10^{-IM \cdot N}i) - W_{fi})\} \cdot (1 - 10^{-IM \cdot N}i) = 0;$$

The value of IB being able to be found as a function of IM from the above equation:

$$IB = \frac{\sum_{i=1}^{n} W_{fi} \cdot (1 - 10^{-IM \cdot N_i})}{\sum_{i=1}^{n}(1 - 10^{-IM \cdot N}i)^2}$$

Similarly, and with the same aim of minimising the square error ($\varepsilon$): the first partial derivative of $\varepsilon$ (Equation (3)) is set equal to zero, this time with respect to the other variable IM, and an equation is obtained with respect to IM with the minimum error of adaptation to the theoretical curve postulated for the cluster of points resulting from the experimental data:

$$\frac{\partial \varepsilon}{\partial IM} = 2 \cdot \sum_{i=1}^{n}\{IB \cdot (1 - 10^{-IM \cdot N}i) - W_{fi})\} \cdot (IB \cdot N_i) \cdot 10^{-IM \cdot N}i) = 0$$

With two possible solutions being obtained:
IB=0, a solution that can be ignored since it is absurd (patient with sliming power=0),
and $$IB = \frac{\sum_{i=1}^{n} W_{fi} \cdot N_i \cdot 10^{-IM \cdot N_i}}{\sum_{i=1}^{n} N_i \cdot (1 - 10^{-IM \cdot N}i) \cdot 10^{-IM \cdot N}i} \quad \text{(Equation 5)}$$

Equating and simplifying the two Equations (4) and (5) (with two unknowns: IB and IM) and considering (for example) that the number of points n is equal to 12 in total, one finally arrives at the following equation which depends solely on IM:

$$\frac{\sum_{i=1}^{n} W_{fi} \cdot N_i \cdot 10^{-IM \cdot N_i}}{\sum_{i=1}^{n} N_i \cdot 10^{-IM \cdot N_i} - \sum_{i=1}^{n} N_i \cdot 10^{-2IM \cdot N_i}} = \quad \text{(Equation 6)}$$

$$\frac{\sum_{i=1}^{n} W_{fi} - \sum_{i=1}^{n} W_{fi} \cdot N_i \cdot 10^{-IM \cdot N_i}}{12 - 2 \cdot \sum_{i=1}^{n} 10^{-IM \cdot N_i} + \sum_{i=1}^{n} 10^{-2IM \cdot N_i}}$$

This equation (which has to be solved by means of successive iterations, preferably with the aid of computing means) enables one to obtain the value of IM (since this is the sole variable) for which the exponential curve fits as closely as possible to the initial cluster of points.

Having obtained that value of IM from Equation (6), and substituting it into Equation (4), one also obtains the value of IB which, together with the value of IM stated earlier, completely determines the exponential curve for accumulated weight loss that provides the best mathematical model for the initial cluster of points.

As already mentioned, Equation (6) has to be solved with a computer by means of a program specifically developed for that purpose.

In order to complete the solution, for each patient equation (6) has had to be solved more than a thousand times, including summations of 12 products, by means of this program.

In order to solve the equation, one merely has to introduce (input) into the computer the weight losses of the patent accumulated over 12 weeks of treatment and one obtains (output) the value of IB and the value of IM for each patient and the sliming treatment that has been followed.

In this way, a quick and easy method is obtained for comparing the efficacy of different treatments and methods for slimming, as well as for separating the different typologies of obese patients into groups for their consideration and later individual study.

The mathematical model developed enables an evaluation to be made quickly and effectively of the efficacy of any anti-obesity treatment, separating the efficacy of the treatment from the factors that depend exclusively on each individual, thereby being of great use when it comes down on selecting among so many types of variations of treatment that have had to be developed for arriving at the treatment that is claimed in this patent application.

Nevertheless, among thousands of patients, due to having a very wide range of values in the asymptote, the mean values of $W_{fi}$ were not very reliable due to the existence of a large scattering of values depending on the asymptote resulting in each case. This led us to confine ourselves solely, as a prior test, to all patients (about 3000) whose asymptote fell between +10% and −10% of the arithmetic mean of all the patients studied (about 30,000 studies during the course of more than 20 years).

This mean asymptote (mean potential for weight loss among all the patients) turned out to correspond to a value of weight loss $W_i$ of 17.78 kg. The arithmetic mean was used because, as the cluster of points was an asymmetric and positive distribution, the mean is higher than the median and the mode.

Moreover, as the asymptote of many patients coincided, in order to simplify things a study was made of their frequencies, applying the following formula for obtaining the arithmetic mean:

$$\overline{x} = \frac{n_1 \cdot x_1 + n_2 \cdot x_2 + \ldots + n_n \cdot x_n}{n_1 + n_2 + \ldots + n_n}$$

The band of +/−10% of the mean value of the asymptote therefore stood at between 16 kg and 19.5 kg. A selection was made of 3000 clinical records whose planning and expectations of weight loss (asymptote) fell between 16 and 19.56 kg, and the accumulated weekly weight losses were noted during the course of 12 weeks, for each patient.

The arithmetic mean of the values obtained experimentally each week was then calculated, which permitted certain values of $W_{fi}$ to be obtained which were used for obtaining IM and IB starting from Equations (6) and (4), respectively. The following values of $W_{fi}$ were obtained:

TABLE IV

Arithmetic mean of the accumulated weight loss in each week for patients within the band +/−10% of the asymptote

| | |
|---|---|
| $W_{f1}$ | 2.75 |
| $W_{f2}$ | 5.74 |
| $W_{f3}$ | 7.25 |
| $W_{f4}$ | 9.30 |
| $W_{f5}$ | 10.85 |
| $W_{f6}$ | 12.22 |
| $W_{f7}$ | 13.80 |
| $W_{f8}$ | 14.10 |
| $W_{f9}$ | 14.75 |
| $W_{f10}$ | 15.35 |
| $W_{f11}$ | 15.75 |
| $W_{f12}$ | 16.00 |

In the event of 12 weeks having passed and, having calculated the values of IM and IB, the weight loss was less than 16 kg, or higher than 19.5 kg, then the specific results of that patient were discarded. So, this concerns the typical method in which the study methods are implemented after having carried out the experiments and the corresponding measurements and having obtained the specific data a posteriori.

Therefore, the mathematical-clinical study comprises three different phases, namely:

In the first phase, the work band was centred by means of a mean asymptotic band and the corresponding $W_{fi}$: with a single standard treatment, the most frequent value of the asymptote, IB, was measured in 3000 patients, thereby obtaining the mean asymptote (17.78 kg) and the asymptotic band in which the work would be carried out henceforth, just by finding the values of +/−10% of the mean asymptote (between 16.00 kg and 17.78 kg). In the same way, during this work phase, the 12 mean values of $W_{fi}$ were obtained for that asymptotic band (band of maximum weight losses weekly accumulated). Putting this another way: for an IB lying between 16.00 kg and 19.56 kg, it is assumed that if, from that asymptotic band certain results are obtained, these will be perfectly able to be extrapolated to other values of the asymptote. In other words: the best possible slimming method for IB=17.78 kg is also the best method for any value of excess weight.

In the second phase, a selection is made of records of patients whose mean prospects of weight loss lie within the chosen band, which permits the same values of $W_{fi}$ to be used at all times, thereby minimising possible margins of error. In other words, applying first the method of mean squares in order to obtain Equations (6) and (4), in order to then confine oneself in this phase to a well defined asymptotic band that encompasses the mean asymptote.

In the third phase, the types of treatments and formulas are chosen that optimise the IM. In other words, a determination is made of which types of treatments, formulas and doses of each component make our treatment the optimum one among all those possible. Of course, the state of the art of each of the components of the formula is known separately (recommended dose or therapeutic windows), though without so far knowing which could be the optimum value of each of those components when mixed in the claimed formula. In this way, the standard treatments used in the development of the claimed formulation were those that really could be more effective and innocuous (always less than the therapeutic window of each component for each of them).

In order to carry out the third phase, the types of treatment and slimming formulations are selected, that optimise the value of the efficacy index, based on various principles which are described in further detail below, and among which the essential aspects are:

the importance of the ratio or principle of macro-micropeptide relay of hypothalamus and hypophysis,
the ratio between the dose of hypothalamus and hypophysis, which must be approximately 1:100,
the ratio between the dose of hypophysis and thyroid, which must be approximately 1:3,
the dose of thyroid, which must not exceed 30 mg,
the dose of hypothalamus need not to exceed 0.2 mg,
the value of IB, which must be 17.78 kg (+/−10%), in other words, between 16 kg and 19.56 kg.

In order to optimise the model of the present invention, slimming formulations were used which contained the essential components hypophysis/hypothalamus/thyroids in the quantities shown below, with which formulations the values of IM shown in table V were obtained.

TABLE V composition of the formulations

| hypothalamus | hypophysis | thyroid | value of IM (x1/1000) |
|---|---|---|---|
| 0.05 mg | 5 mg | 15 mg | 7.87 |
| 0.05 mg | 5 mg | 30 mg | 7.90 |
| 0.05 mg | 10 mg | 15 mg | 8.02 |
| 0.05 mg | 10 mg | 30 mg | 8.05 |
| 0.05 mg | 20 mg | 15 mg | 8.07 |
| 0.05 mg | 20 mg | 30 mg | 8.14 |
| 0.1 mg | 5 mg | 15 mg | 8.10 |
| 0.1 mg | 5 mg | 30 mg | 8.13 |
| 0.1 mg | 10 mg | 15 mg | 8.12 |
| 0.1 mg | 10 mg | 30 mg | 8.26 |
| 0.1 mg | 20 mg | 15 mg | 8.15 |
| 0.1 mg | 20 mg | 30 mg | 8.18 |
| 0.2 mg | 5 mg | 15 mg | 8.11 |
| 0.2 mg | 5 mg | 30 mg | 8.16 |
| 0.2 mg | 10 mg | 15 mg | 8.03 |
| 0.2 mg | 10 mg | 30 mg | 8.07 |
| 0.2 mg | 20 mg | 15 mg | 7.92 |
| 0.2 mg | 20 mg | 30 mg | 7.99 |

For all the combinations of the essential components of the formulation, good values were obtained for IM, the best of them—IM=8.26—being obtained with the formulation containing 0.1 mg of hypothalamus, 10 mg of hypophysis and 30 mg of thyroid.

It has been possible to conclude that the value of the constant IM—the efficacy index—is essential for the preparation of a slimming formulation.

In this way, the system and procedure of the present invention provide a useful tool for comparing the efficacy of different slimming treatments, as well as for separating the different types of obese patient, in such a way that an individual study can then be conducted.

The third objective of the present invention is therefore a formulation whose essential components and the quantities in which they are present have been obtained as a result of the application of the procedure described above.

From the study of 30000 patients and the application of the described procedure, the formulation of the present invention has been arrived at, based on the values of IM obtained and founded on a series of principles that are described below:

1. Principle of neuro-endocrine balance, or principle of relay action of the hypothalamic-hypophyseal axis. The basis of this principle lies in the fact that the information in the encephaloa is effected by means of neurotransmitters at the neurone synapse level. These neurotransmitters are generally micropeptides. There exists a reserve of those micropeptides, on which the hypothalamus also feeds, in such a way that the hypothalamus captures them in order to synthesise hypothalamic releasing factors and which act as messengers for controlling hormone synthesis in the hypophysis (macropeptide hormones).

In the formulation according to the present invention, very special consideration is given to the molecular weights of the releasing factors of the hypothalamus and the molecular weights of the hormones of the anterior lobe of the hypophysis. The necessary quantity of hypothalamus powder in the formulation, and of hypophysis powder, calculated according to the results of the procedure described above and bearing in mind the present principle of endocrine balance, lies between 0.01 mg and 0.5 mg for hypothalamus powder, and 1 mg to 30 mg for hypophysis powder. By means of applying the procedure object of the present invention, one arrives at the preferred quantity of hypothalamus powder compared to hypophysis powder, which must be 0.1 mg for hypothalamus powder and 10 mg for hypophysis powder. Therefore, these are the quantities in which these two basic components of the formulation of the present invention will preferably be present.

So, according to the principle of the relay effect of the hypothalamic-hypophyseal axis, and according to the principle of natural satiation of appetite, the formulation of the present invention contains hypothalamus powder and hypophysis powder. The proportions in which they are present have been calculated according to the mean molecular weights and the primary and secondary structures of the hypothalamic releasing factors, along with the molecular weights and structures of the hormones of the glandular hypophysis, as well as considering the results of the application of the system and procedure of the present invention.

2. Principle of interglandular balance. The endocrine cascade is considered as a system integrated and interrelated by means of bio-feedback mechanisms. It is not possible to treat obesity solely by means of thyroxine or thyroid extracts, owing to the close interrelation that the glandular secretion mechanisms have. Serious endocrine maladjustments can occur with blockage of the secretion of hypophyseal TSH and even generalised blockages of the hypophysis, which can cause dysfunctions in other glands such as the pancreas, the suprarenals or the gonads, with the consequent problems of health and pathologies at the levels of those glands. By virtue of this interrelation, contributions of extract of a single gland cannot be supplied without supplying contributions of the others. Nevertheless, account must be taken of the way in which proteins are absorbed via the intestinal tract, which is not amino acid to amino acid but instead by means of passage via the digestive barrier of real polypeptide microchains.

Nor is it a question of using the same quantity of each opotherapic extract, since not all hormones or hypothalamic releasing factors have the same molecular weight nor the same primary and secondary structure.

Bearing in mind the complex intestinal absorption of peptides, as well as the major differences in primary and secondary structure of hormones and of releasing factors, with the application of the procedure of the present invention it has been possible to transfer the results obtained for each patient with different mixtures and, by means of successive practical trials, adjust the quantities according to the results of the procedure. In other words, the interglandular balance has been achieved by means of the method of successive trials, in which the real quantities of opotherapic extracts that must be present in the formulation have been adjusted.

Other essential components of the formulation of the present invention, according to the described principle of endocrine system integrated and interrelated by means of bio-feedback mechanisms, are:
  thyroid powder
  suprarenal cortex powder and
  pancreas powder.

The quantities in which these components are present in the formulation of the present invention are calculated according to the quantity of hypophysis powder, as stated above, and bearing in mind the characteristics of the hormone segregated by each gland.

The formulation of the present invention can also contain gonad powder, in other words testicle powder (in men) or ovary powder (in women).

Figure 5:
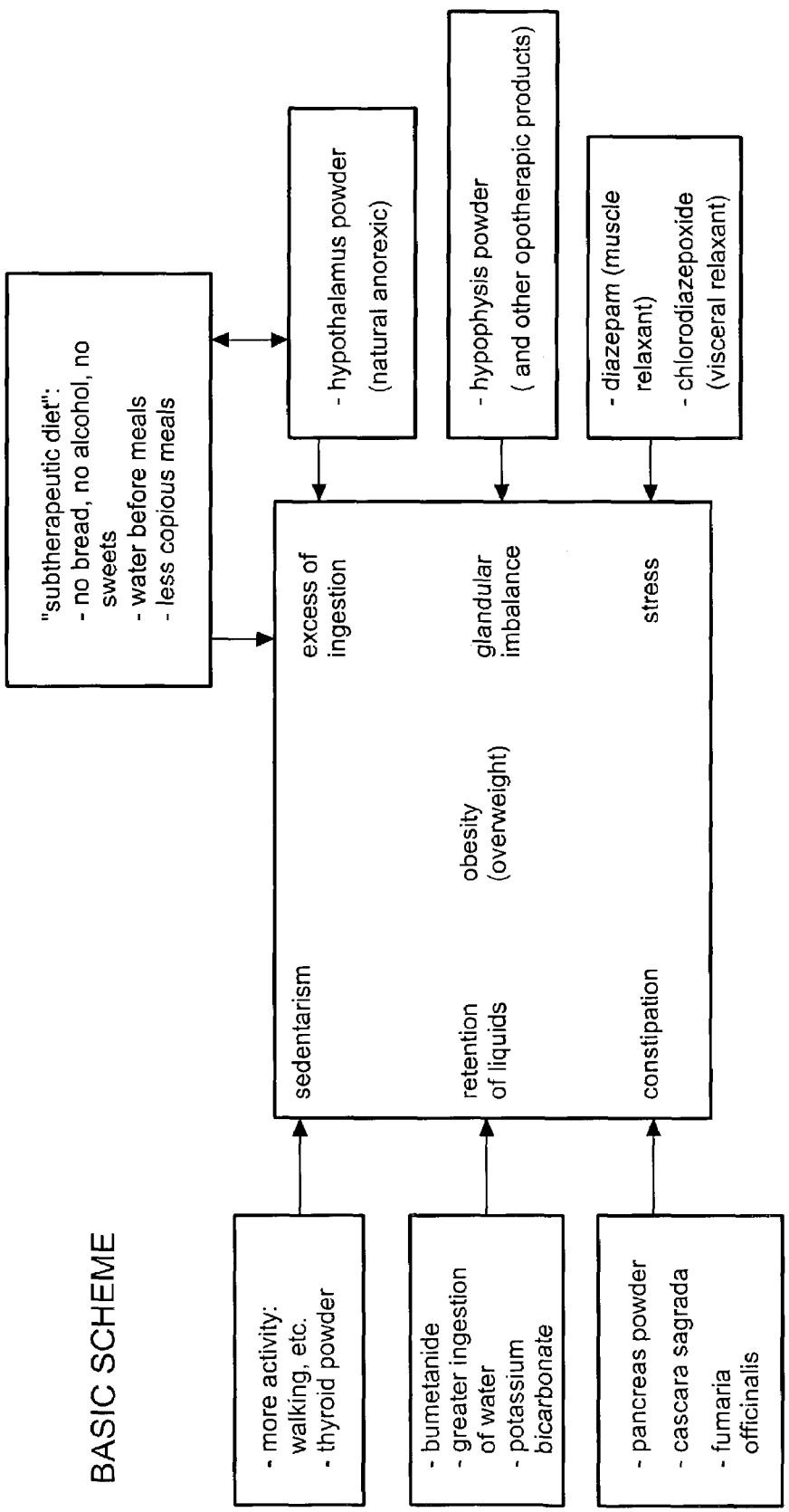
FIG. 5 shows some factors that influence obesity and its relation with the components of the formulation of the present invention which act against the negative effects produced by those factors.

3 The principle of synergy with dispersion of secondary effects. The quantity of drugs present in the formulation of the present invention lies below the therapeutic limits. As is known, in the treatment of illnesses with various drugs, these act with their main action on the problem and producing side effects (some are metabolised by the liver, others by the kidneys, others by the intestines, etc.), which have an effect on different organs, thereby the undesired effect is minimised and the objective of curing the illness is strengthened by synergy. Therefore, the synergy of multiple therapeutic agents in the case of treating obesity must not be ignored. Some of the factors influencing obesity are sedentarism, liquid retention, constipation, excess ingestion, glandular imbalance, stress. The diagram shown in FIG. 5 shows these factors that influence obesity and their relation with the components of the formulation of the present invention which act against the negative effects produced by those factors.

According to the basic diagram shown, it will be necessary to increase or decrease the quantity of one or more of the components of the formulation in the dose depending on the stated aetiological factors.

All these components mentioned in the diagram, such as an opotherapic product, a plant extract, a laxative, an anorexic, etc., are fairly different from each other and have very different side effects, though their main action is directed towards treatment of obesity.

Among the components of a formulation according to the present invention, diuretics can be present, which are very necessary at the start of a slimming treatment. These will preferably be present in the formulation in very low quantities. In the case of women they are also useful on premenstrual days since, although the body retains liquids prior to menstruation and tends to eliminate them afterwards, the amount retained on premenstrual days is appreciably greater than the amount eliminated after menstruation. In some cases, with a lot of sedentarism, this difference can be a real cause of obesity since the liquids accumulated in the tissues open up gaps with are exploited by adipocytes in order to become hypertrophied.

Diet can also be used as a therapeutic agent against obesity, and will be practised in a moderate way in "small doses". This means eliminating bread, sweets, alcohol, and ingesting smaller quantities of other foods, though without measuring.

4. Principle of homeomorphia and homeobaria. This principle, on which the formulation of the present invention also rests, is based on the hypothalamic control over body shape and weight. At the start of recording their excess weight, some patients observe a deformation of the body. This fact is not surprising if it is related to the exhaustion of the reserve of neurotransmitters due to excessive stress. It has been stated earlier that when the hypothalamus cannot properly capture the neurotransmitters it needs from the encephalic reserve, then it starts to function badly. Just as there exist homeostatic nuclei of hunger, satiation, hyperthermia, hypoglucemia, etc., so there can also exist in the hypothalamus control nuclei over body shape, in order to achieve an energy homeostasia of the entropic type or with regard to tissue. The existence can therefore be postulated of a homeomorphia in charge of controlling the hypothalamus and if the stated nuclei exist, then a homeobaria could also occur which is also dependent on the control of the hypothalamus.

It is known that the hypothalamus receives signals coming from almost all possible sources of the central nervous system, and when a person suffers pain, part of the pain signal is transmitted to the hypothalamus. In the same way, when a person has exciting or depressing ideas, part of the signals are transmitted to the hypothalamus. It has been confirmed that the hypothalamus is a meeting point for information related to the well-being of the body.

5. Principle of hypothalamic satiation of appetite. The formulation of the present invention is also based on the acknowledged fact that satiation of appetite is governed by the ventromedial nuclei of the hypothalamus, and that the sensation of hunger derives from its ventrolateral nuclei. It is also known that considerable weight increases sometimes occur as a consequence of psychological traumas. The hypothalamus therefore receives information from the nerve centres where the suffering due to these traumas is being processed.

In the preparation of opotherapic products, moreover, the hypothalamus powder used does not contain material from the ventrolateral regions, which are eliminated from the hypothalamuses of animals before being crushed, purified and dried. Therefore, this hypothalamus powder only contains material from the ventromedial nuclei and, being present in a formulation for a slimming treatment, they stimulate the hypothalamic nuclei for satiation in natural way. In the formulation of the present invention, the hypothalamus powder is present in small quantities, so that no side effects of hyperexcitation, arterial hypertension or others take place.

6. Principle of balanced elimination. The aim is to aid diuresis and defecation. Retention of liquids in some parts of the body and intestinal constipation are factors that must be borne in mind in all treatments of obesity. There exist many diuretic plant species, such as *Arenaria rubra* or *Equisetum arvense*. Nevertheless, in serious situations of liquid retention even using both simultaneously does not give good results. These cases occur when the kidneys are "lazy kidneys". It is then more advisable to use a diuretic in very small quantities.

Optionally, therefore, the formulation of the present invention can include some drugs and plants intended to facilitate during treatment the elimination of retained liquids—increasing the diuresis—and also faecal elimination, avoiding intestinal constipation. Bumetanide is preferably used as a very reliable diuretic in prolonged treatments at very low doses.

Similarly, the plants used in an optional way accelerate the digestion and intestinal transmit. As far as intestinal constipation is concerned, use can be made of a medicinal plant such as *Rhamnus pursiana*, or cascara sagrada, as a laxative, and in some especially complicated cases, an infusion of *Cassia angustifolia*. The quantity of *Rhamnus pursiana* present in the formulation is preferably between 15 and 20 mg.

As a digestive tonic or accelerator of digestion, use is optionally and preferably made of a nebulised extract of *Fumaria officinalis*. The amount of *Fumaria officinalis* in the formulation is between 50 and 70 mg.

The formulation of the present invention can also include some mineral vitamin complex because, according to the principle of synergy of multiple agents at very low doses and with dispersion of side effects, a moderate diet is included in the treatment and therefore bread, alcohol, sweets, pizzas and nuts are categorically banned.

The formulation of the present invention can also include, according to the described principle of homeomorphia and homeobaria, very low doses of benzodiazepines in order to eliminate residual muscular tension, both of smooth fibre and of striated fibre. These benzodiazepines are preferably chlorodiazepoxide for smooth fibre and diazepam for striated fibre. No type of cross-reaction has been observed of the pharmacological agents used, neither of simple type nor of the recombined type.

The formulation of the present invention can also include an anorexic, according to the principle of reduction of appetite, both in natural form by means of hypothalamus powder and in pharmacological form. When administered in pharmacological form, this anorexic is preferably diethylpropion (anfepramone or fluoxetine in a quantity between 10 and 20 mg).

Therefore, the formulation according to the present invention comprises at least:
  hypothalamus powder in a quantity between 0.01 and 0.5 mg,
  hypophysis powder in a quantity between 1 and 30 mg,
  thyroid powder in a quantity between 10 and 40 mg,
  suprarenal cortex powder and pancreas powder in a proportion of 1:4.

According to an alternative embodiment, a formulation comprises at least:
  hypothalamus powder in a quantity between 0.01 and 0.5 mg,
  hypophysis powder in a quantity between 1 and 30 mg,
  thyroid powder in a quantity between 10 and 40 mg,
  suprarenal cortex powder and pancreas powder in a proportion of 1:4
  a laxative and
  a digestive tonic.

The laxative and the digestive tonic can be present in the formulation as plant extracts in a total quantity between 70 mg and 90 mg.

The plant extracts are preferably:
*Fumaria officinalis* as a digestive tonic, which is present in a quantity between 50 and 70 mg.
*Rhamnus pursiana* as a laxative in a quantity between 15 and 20 mg.

According to an additional alternative embodiment, a formulation comprises at least:
hypothalamus powder in a quantity between 0.01 and 0.5 mg,
hypophysis powder in a quantity between 1 and 30 mg,
thyroid powder in a quantity between 10 and 40 mg,
suprarenal cortex powder and pancreas powder in a proportion of 1:4
a laxative,
a digestive tonic and
at least one muscle relaxant.

In the formulation of the present invention, the muscle relaxant is preferably selected from between:
diazepam as striated fibre relaxant, in a quantity between 1.0 and 2.5 mg,
chlorodiazepoxide as smooth fibre relaxant, in a quantity between 1.0 and 2.5 mg, and
a mixture of both.

According to an additional alternative embodiment, a formulation comprises at least:
hypothalamus powder in a quantity between 0.01 and 0.5 mg,
hypophysis powder in a quantity between 1 and 30 mg,
thyroid powder in a quantity between 10 and 40 mg,
suprarenal cortex powder and pancreas powder in a proportion of 1:4
plant extracts,
at least one muscle relaxant, and
a diuretic The diuretic is preferably present in a quantity between 0.2 and 0.5 mg.

The diuretic is preferably bumetanide and is present in a quantity between 0.2 and 0.5 mg.

An additional alternative embodiment refers to a formulation which includes at least:
hypothalamus powder in a quantity between 0.01 and 0.5 mg,
hypophysis powder in a quantity between 1 and 30 mg,
thyroid powder in a quantity between 10 and 40 mg,
suprarenal cortex powder and pancreas powder in a proportion of 1:4-plant extracts in a quantity between 70 mg and 90 mg,
a diuretic in a quantity between 0.2 and 0.5 mg,
at least one muscle relaxant, and
potassium bicarbonate in a quantity between 100 and 140 mg.

According to a preferred embodiment, a formulation comprises at least:
hypothalamus powder in a quantity of 0.01 mg,
hypophysis powder in a quantity of 10 mg,
thyroid powder in a quantity of 30 mg, and
suprarenal cortex powder and pancreas powder in a proportion of 1:4.

A second preferred alternative embodiment refers to a formulation which comprises:
hypothalamus powder in a quantity of 0.01 mg,
hypophysis powder in a quantity of 10 mg,
thyroid powder in a quantity of 30 mg,
suprarenal cortex powder in a quantity of 20 mg,
pancreas powder in a quantity of 80 mg
*Fumaria officinalis* as a digestive tonic in a quantity between 50 and 70 mg,
*Rhamnus pursiana* as a laxative in a quantity between 15 and 20 mg,
diazepam in a quantity between 1.0 and 2.5 mg,
chlorodiazepoxide in a quantity between 1.0 and 2.5 mg,
bumetanide in a quantity between 0.2 and 0.5 mg, and
potassium bicarbonate in a quantity between 100 and 140 mg.

Moreover, the formulation of the present invention can include in any of its embodiments and as an option an anorexic in a quantity between 10 and 30 mg. This anorexic can be anfrepramone, preferably in a quantity between 20 and 30 mg or fluoxetine in a quantity between 10 and 20 mg.

The present invention also refers to a galenic form for the oral administration of a formulation as has been defined above, which includes at least:
hypothalamus powder in a quantity between 0.01 and 0.5 mg,
hypophysis powder in a quantity between 1 and 30 mg,
thyroid powder in a quantity between 10 and 40 mg,
suprarenal cortex powder and pancreas powder in a proportion of 1:4

This galenic form is preferably selected from among capsules, tablets, pills and pastilles.

In a preferred embodiment a galenic form for the administration of a formulation comprises at least:
hypothalamus powder in a quantity of 0.01 mg,
hypophysis powder in a quantity of 10 mg,
thyroid powder in a quantity of 30 mg,
suprarenal cortex powder in a quantity of 20 mg,
pancreas powder in a quantity of 80 mg
*Fumaria officinalis* as a digestive tonic in a quantity between 50 and 70 mg,
*Rhamnus pursiana* as a laxative in a quantity between 15 and 20 mg,
diazepam in a quantity between 1.0 and 2.5 mg,
chlorodiazepoxide in a quantity between 1.0 and 2.5 mg,
bumetanide in a quantity between 0.2 and 0.5 mg, and
potassium bicarbonate in a quantity between 100 and 140 mg.

In an even more preferred embodiment a galenic form for the administration of a formulation comprises:
capsules of a first type (format 2) which contain:
hypothalamus powder in a quantity of 0.01 mg,
thyroid powder in a quantity of 30 mg,
diazepam in a quantity between 1.0 and 2.5 mg,
chlorodiazepoxide in a quantity between 1.0 and 2.5 mg,
bumetanide in a quantity between 0.2 and 0.5 mg, and
capsules of a second type (format 1) which contain:
hypophysis powder in a quantity of 10 mg,
suprarenal cortex powder in a quantity of 20 mg,
pancreas powder in a quantity of 80 mg
*Rhamnus pursiana* as a laxative in a quantity between 15 and 20 mg,
*Fumaria officinalis* as a digestive tonic in a quantity between 50 and 70 mg, and
potassium bicarbonate in a quantity between 100 and 140 mg.

A galenic form for the administration of a formulation preferably comprises:
capsules of a first type (format 2) which contain:
hypothalamus powder in a quantity of 0.1 mg,
thyroid powder in a quantity of 30 mg,
diazepam in a quantity of 1.5 mg, chlorodiazepoxide in a quantity of 1.5 mg, and
bumetanide in a quantity of 0.3 mg, and
capsules of a second type (format 1) which contain:
hypophysis powder in a quantity of 10 mg,
suprarenal cortex powder in a quantity of 20 mg,
pancreas powder in a quantity of 80 mg
*Rhamnus pursiana* and *Fumaria officinalis* in a total quantity of 80 mg, and
potassium bicarbonate in a quantity of 100 mg.

The formulation of the present invention will preferably be taken twice a day, always between meals. It will preferably be taken two hours before the main meal and two or three hours before dinner. It is taken with a fair amount of water in order to accelerate the gastric transmit which, due to being acid, greatly alters the animal and plant extracts, and so that the formulation reaches the alkaline intestinal tract as quickly as possible.

The present formulation presents the following advantages with respect to other formulations of the state of the art:

no adverse reactions have ever been observed, on account of the small doses of each component;

not just a slimming effect is obtained but also euphoria and well-being are observed, alleviation of allergy problems, alleviation of rheumatological problems, alleviation of menstrual problems, alleviation of digestive problems, alleviation of sleeping problems, drop in cholesterol, triglycerides and uric acid, alleviation of skin problems and correction of arterial hypertension.

Some of these advantages derive from the actual effect of losing weight and others are predictable effects of the formulation itself.

EXAMPLES

Example 1

By the usual methods known in the art, a formulation is prepared comprising:
0.01 mg of hypothalamus powder,
10 mg of hypophysis powder,
30 mg of thyroid powder,
20 mg of suprarenal cortex powder,
80 mg of pancreas powder,
15 mg of testicle powder,
65 mg of *Fumaria officinalis*,
17 mg of *Rhamnus pursiana*,
1.5 mg of diazepam,
1.5 mg of chlorodiazepoxide,
0.3 mg of bumetanide, and
100 mg of potassium bicarbonate, Example 2

By the usual methods known in the art, a formulation similar to that of example 1 is prepared, but with 15 mg of ovary powder instead of 15 mg of testicle powder:

Example 3

By the usual methods known in the art, a galenic form is prepared comprising:
capsules of format 2 which contain:
hypothalamus powder in a quantity of 0.1 mg,
thyroid powder in a quantity of 30 mg,
diazepam in a quantity of 1.5 mg,
chlorodiazepoxide in a quantity of 1.5 mg, and
bumetanide in a quantity of 0.3 mg, and
capsules of format 1 which contain:
hypophysis powder in a quantity of 10 mg,
suprarenal cortex powder in a quantity of 20 mg,
pancreas powder in a quantity of 80 mg
65 mg of *Fumaria officinalis*,
17 mg of *Rhamnus pursiana*, and
100 mg of potassium bicarbonate.

The invention claimed is:

1. A galenic form for the administration of a formulation comprising at least:
hypothalamus powder in a quantity between 0.01 and 0.5 mg,
hypophysis powder in a quantity between 1 and 30 mg,
thyroid powder in a quantity between 10 and 40 mg,
suprarenal cortex powder and pancreas powder in a proportion of 1:4, said galenic form being adapted for oral administration.

2. A galenic form according to claim 1, which is selected from capsules, tablets, pills and pastilles.

* * * * *